US006627437B1

United States Patent
Traboni

(10) Patent No.: US 6,627,437 B1
(45) Date of Patent: Sep. 30, 2003

(54) GBV SEQUENCE

(75) Inventor: Cinzio Traboni, Rome (IT)

(73) Assignee: Istituto di Ricerche di Biologia Molecolare P. Angeletti S.p.A., Pomezia (IT)

(*) Notice: Subject to any disclaimer, the term of this patent is extended or adjusted under 35 U.S.C. 154(b) by 0 days.

(21) Appl. No.: 09/579,302

(22) Filed: May 25, 2000

(30) Foreign Application Priority Data

May 27, 1999 (GB) .............................................. 9912432

(51) Int. Cl.[7] ........................ C12N 15/74; C07H 21/02; C07H 21/04

(52) U.S. Cl. ................ 435/320.1; 536/23.1; 536/23.72; 536/24.1; 536/24.2; 435/235.1; 435/252.3; 435/325; 435/363

(58) Field of Search .............................. 536/23.1, 23.72, 536/24.1, 24.2; 435/235.1, 325, 363, 320.1, 252.3

(56) References Cited

FOREIGN PATENT DOCUMENTS

WO   WO 00/75337   * 12/2000

OTHER PUBLICATIONS

Caselmann, Wolfgang H., "HBV and HDV replication in experimental models: effect of interferon." Antiviral Research 1994; 24: 121–129.
Deinhardt, M.D., F., A. W. Holmes, M.D., R. B. Capps, M.D., and H. Popper, M.D., "Studies on the Transmission of Human Viral Hepatitis to Marmoset Monkeys." Presbyterian–St. Luke's Hospital et al., 1996: 673–688.
Emerson, Suzanne U., et al., "cDNA Clone of Hepatitis A Virus Encoding a Virulent Virus: Induction of Viral Hepatitis by Direct Nucleic Acid Transfection of Marmosets." Journal of Virology 1992; vol. 66, No. 11: 6649–6654.
Honda, Masao, et al., "A Phylogenetically Conserved Stem–Loop Structure at the 5' Border of the Internal Ribosome Entry Site of Hepatitis C Virus Is Required for Cap–Independent Viral Translation." Journal of Virology 1999; vol. 73, No. 2: 1165–1174.
Yanagi et al., Transcripts of a Chimeric cDNA Clone of Hepatitis C Virus Genotype 1b Are Infectious in Vivo. Virology 244:161–172, 1998.*
Bukh et al., Toward a Surrogate Model for Hepatitis C Virus: An Infectious Molecular Clone of the GB Virus–B Hepatitis Agent. Virology 262:470–478, 1999.*
Dienstag et al., Virus–like particles and GB agent hepatitis. Nature 264:260–261, 1976.*
Ito, Takayoshi, et al., "The 3'–Untranslated Region of Hepatitis C Virus RNA Enhances Translation from an Internal Ribosomal Entry Site." Journal of Virology 1998; vol. 72, No. 11: 8789–8796.

Kolykhalov, Alexander A., et al., "Transmission of Hepatitis C by Intrahepatic Inoculation with Transcribed RNA." Science 1997; 277: 570–574.
Kolykhalov, Alexander A., et al., "Identification of a Highly Conserved Sequence Element at the 3' Terminus of Hepatitis C Virus Genome RNA." Journal of Virology 1996; vol. 70, No. 6: 3363–3371.
Lemon, Stanley M., and Masao Honda, "Internal Ribosome Entry Sites within the RNA Genomes of Hepatitis C Virus and Other Flaviviruses." Virology 1997; 8: 274–288.
Muerhoff, A. Scott, et al., "Genomic Organization of GB Viruses A and B: Two New Members of the Flaviviridae Associated with GB Agent Hepatitis." Journal of Virology 1995; vol. 69, No. 9: 5621–5630.
Ohba, Ken–ichi, et al., "Evolutionary relationship of hepatitis C, pesti–, flavi–, plantviruses, and newly discovered GB hepatitis agents." FEBS Letters 1996: 232–234.
Pilot–Matias, Tami J., et al., "Identification of Antigenic Regions in the GB Hepatitis Viruses GBV–A, GBV–B, and GBV–C." Journal of Medical Virology 1996; 48: 329–338.
Scarselli, Elisa, et al., "GB Virus B and Hepatitis C Virus NS3 Serine Proteases Share Substrate Specificity." Journal of Virology 1997; vol. 71, No. 7: 4985–4989.
Schlauder, George G., et al., "Molecular and Serologic Analysis in the Transmission of the GB Hepatitis Agents." Journal of Medical Virology 1995; 46: 81–90.
Schlauder, George G., et al., "Origin of GB–hepatitis viruses." The Lancet 1995; 346: 447–448.
Shimizu, Yohko K., et al., "Early events in hepatitis C virus infection of chimpanzees." Proc. Natl. Acad. Sci. 1990; 87: 6441–6444.
Simons, John N., et al., "The GB Viruses: Isolation, Characterization, Diagnosis and Epidemiology." Viral Hepatitis Reviews 1996; vol. 2, No. 4: 229–246.
Simons, John N., et al., "Identification of two flavivirus–like genomes in the GB hepatitis agent." Proc. Natl. Acad. Sci. 1995; 92: 3401–3405.
Simons, John N., et al., "Isolation of novel virus–like sequences associated with human hepatitis." Nature Medicine 1995; vol. 1, No. 6: 564–569.
Tanaka, Torahiko, et al., "A Novel Sequence Found at the 3' Terminus of Hepatitis C Virus Genome." Biochemical and Biophysical Research Communications 1995; vol. 215, No. 2: 744–749.
Tsuchihara, Katsuya, et al., "Specific Interaction of Polypyrimidine Tract–Binding Protein with the Extreme 3'–Terminal Structure of the Hepatitis C Virus Genome, the 3'X." Journal of Virology 1997; vol. 71, No. 9: 6720–6726.

(List continued on next page.)

Primary Examiner—Donna C. Wortman
(74) Attorney, Agent, or Firm—Sheldon O. Heber; Jack L. Tribble

(57) ABSTRACT

Hitherto undiscovered 3' sequence of GBV confers infectivity in tamarins on otherwise non-infective GBV genome. HCV sequences may be substituted within an infective GBV genome to provide for in vivo assays for agents able to modulate HCV activity.

24 Claims, 6 Drawing Sheets

OTHER PUBLICATIONS

Yanagi, Masayuki, et al., "Transcripts from a single full–length cDNA clone of hepatitis C virus are infectious when directly transfected into the liver of a chimpanzee." Proc. Natl. Acad. Sci. 1997; 94: 8738–8743.

Yanagi, Masayuki, et al., "In vivo analysis of the 3' untranslated region of the hepatitis C virus after in vivo mutagenesis of an infectious cDNA clone." Proc. Natl. Acad. Sci. 1999; 96: 2291–2295.

Zuckerman, Arie J., "The new GB hepatitis viruses." The Lancet 1995; 345: 1453–1454.

* cited by examiner

```
                                                    1      10
AGGGCAGCGGCAACAGGGGAGACCCCGGGCTTAACGACCCCGCCGATGTGAGTTTGGCGA
         30                  50                  70
CCATGGTGGATCAGAACCGTTTCGGGTGAAGCCATGGTCTGAAGGGGATGACGTCCCTTC 90                 110                 130
TGGCTCATCCACAAAAACCGTCTCGGGTGGGTGAGGAGTCCTGGCTGTGTGGGAAGCAGT

150           ⇓   170                 190
CAGTATAATTCCCGTCGTGTGTGGTGACGCCTCACGACGTACTTGTCCGCTGTGCAGAGC 210                 230                 250
GTAGTACCAAGGGCTGCACCCCGGTTTTTGTTCCAAGCGGAGGGCAACCCCCGCTTGGAA

259
TTAAAAACT
```

Fig. 3

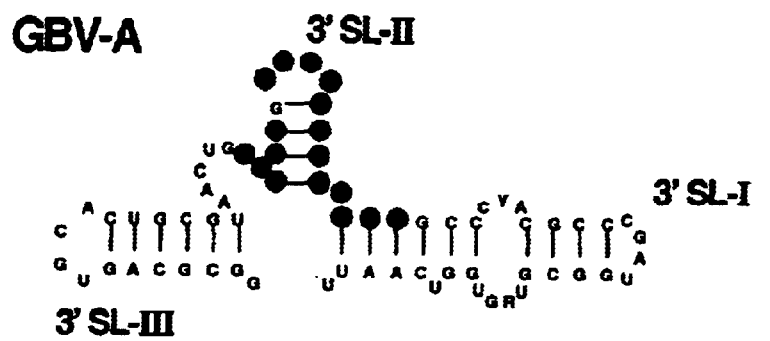
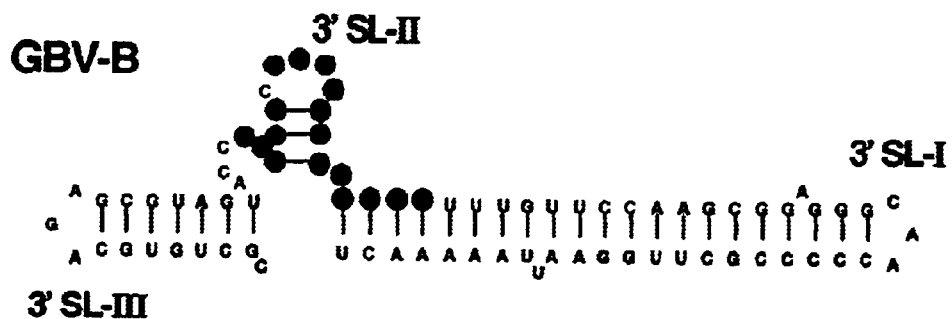
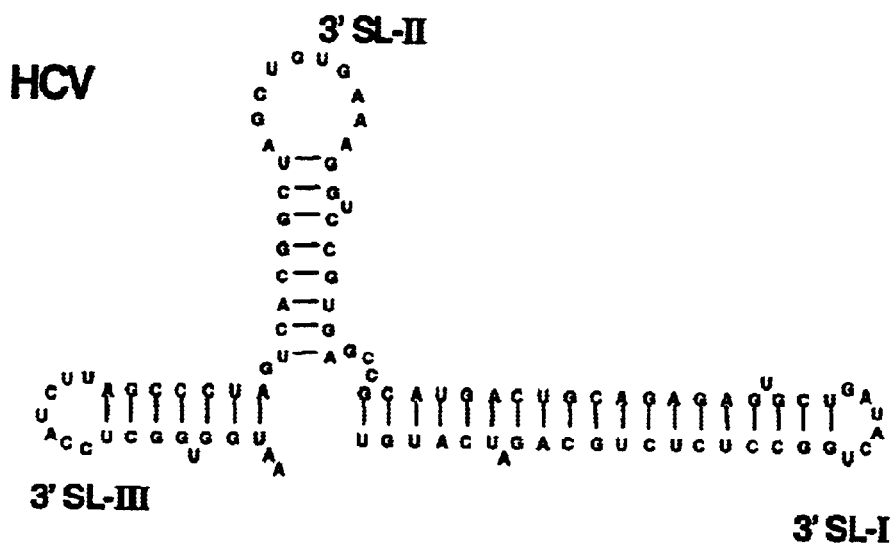
Fig. 4B

SEQUENCE LISTING

<160> NUMBER OF SEQ ID NOS: 16

<210> SEQ ID NO 1
<211> LENGTH: 309
<212> TYPE: DNA
<213> ORGANISM: GBV-B-like virus
<220> FEATURE:
<221> NAME/KEY: 3'UTR
<222> LOCATION: (1)..(309)
<223> OTHER INFORMATION: cDNA complementary to the last 49 published
      3'UTR nucleotides of GBV-B plus a novel nucleotide (C) in
      position 44 and 259 novel nucleotide sequence at the 3' end.

<400> SEQUENCE: 1
agggcagcgg caacagggga gaccccgggc ttaacgaccc cgccgatgtg agtttggcga     60
ccatggtgga tcagaaccgt ttcgggtgaa gccatggtct gaaggggatg acgtcccttc    120
tggctcatcc acaaaaaccg tctcggggtgg gtgaggagtc ctggctgtgt gggaagcagt   180
cagtataatt cccgtcgtgt gtggtgacgc ctcacgacgt acttgtccgc tgtgcagagc    240
gtagtaccaa gggctgcacc ccggttttg ttccaagcgg agggcaaccc ccgcttggaa     300
ttaaaaact                                                            309

<210> SEQ ID NO 2
<211> LENGTH: 259
<212> TYPE: RNA
<213> ORGANISM: GBV-B-like virus

<400> SEQUENCE: 2
aguuuggcga ccauggugga ucagaaccgu uucggugaa gccauggucu gaaggggaug      60
acgucccuuc uggcucaucc acaaaaaccg ucucgggugg gugaggaguc cuggcugugu    120
gggaagcagu caguauaauu cccgucgugu gugugacgc cucacgacgu acuuguccgc    180
ugugcagagc guaguaccaa gggcugcacc ccgguuuuug uuccaagcgg agggcaaccc    240
ccgcuuggaa uuaaaaacu                                                 259

<210> SEQ ID NO 3
<211> LENGTH: 259
<212> TYPE: RNA
<213> ORGANISM: GBV-B-like virus

<400> SEQUENCE: 3
aguuuuuaau uccaagcggg gguugcccuc cgcuuggaac aaaaaccggg gugcagcccu     60
ugguacuacg cucugcacag cggacaagua cgucgugagg cgucaccaca cacgacggga    120
auuauacuga cugcuucccca cacagccagg acuccucacc caccccgagac gguuuuugug   180 gaugagccag aagggacguc auccccuuca gaccauggcu ucacccgaaa cgguucugau    240
ccaccauggu cgccaaacu                                                 259

<210> SEQ ID NO 4
<211> LENGTH: 259
<212> TYPE: DNA
<213> ORGANISM: GBV-B-like virus
<220> FEATURE:
<221> NAME/KEY: 3'UTR
<222> LOCATION: (1)..(259)
<223> OTHER INFORMATION: cDNA of positive strand 3'UTR of GBV-B

<400> SEQUENCE: 4
agtttggcga ccatggtgga tcagaaccgt ttcgggtgaa gccatggtct gaaggggatg     60

```
acgtcccttc tggctcatcc acaaaaaccg tctcgggtgg gtgaggagtc ctggctgtgt      120
gggaagcagt cagtataatt cccgtcgtgt gtggtgacgc ctcacgacgt acttgtccgc      180
tgtgcagagc gtagtaccaa gggctgcacc ccggtttttg ttccaagcgg agggcaaccc      240
ccgcttggaa ttaaaaact                                                   259

<210> SEQ ID NO 5
<211> LENGTH: 259
<212> TYPE: DNA
<213> ORGANISM: GBV-B-like virus
<220> FEATURE:
<221> NAME/KEY: 3'UTR
<222> LOCATION: (1)..(259)
<223> OTHER INFORMATION: cDNA of negative strand 3'UTR of GBV-B

<400> SEQUENCE: 5
agtttttaat tccaagcggg ggttgccctc cgcttggaac aaaaaccggg gtgcagccct       60
tggtactacg ctctgcacag cggacaagta cgtcgtgagg cgtcaccaca cacgacggga      120
attatactga ctgcttccca cacagccagg actcctcacc cacccgagac ggttttttgtg    180 gatgagccag aagggacgtc atccccttca gaccatggct tcacccgaaa cggttctgat      240
ccaccatggt cgccaaact                                                   259

<210> SEQ ID NO 6
<211> LENGTH: 26
<212> TYPE: RNA
<213> ORGANISM: Artificial Sequence
<220> FEATURE:
<223> OTHER INFORMATION: Description of Artificial Sequence:
      oligonucleotide primer
<221> NAME/KEY: primer_bind
<222> LOCATION: (1)..(26)
<223> OTHER INFORMATION: RNA oligonucleotide

<400> SEQUENCE: 6
aaacccuugg acugcgacgg cugcga                                           26

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer
      complementary to part of seq 98094
<221> NAME/KEY: primer_bind
<222> LOCATION: Complement(1)..(21)
<223> OTHER INFORMATION: Primer complementary to the RNA oligo 96934

<400> SEQUENCE: 7
gcagccgtcg cagtccaagg g                                                21

<210> SEQ ID NO 8
<211> LENGTH: 20
<212> TYPE: DNA
<213> ORGANISM: GBV-B-like virus
<220> FEATURE:
<221> NAME/KEY: 3'UTR
<222> LOCATION: (1)..(20)
<223> OTHER INFORMATION: Primer for the 3'UTR sequence in position
      190-171 (?? 185-166)

<400> SEQUENCE: 8
gcacagcgga caagtacgtc                                                  20
```

-continued

<210> SEQ ID NO 9
<211> LENGTH: 22
<212> TYPE: DNA
<213> ORGANISM: GBV-B-like virus
<220> FEATURE:
<221> NAME/KEY: primer_bind
<222> LOCATION: (1)..(22)
<223> OTHER INFORMATION: Primer SGB54 for region 8481-8502

<400> SEQUENCE: 9
ggattgggta tctaatacat ca                                              22

<210> SEQ ID NO 10
<211> LENGTH: 22
<212> TYPE: DNA
<213> ORGANISM: GBV-B-like virus
<220> FEATURE:
<221> NAME/KEY: primer_bind
<222> LOCATION: (1)..(22)
<223> OTHER INFORMATION: Primer SGB56 for region 8801-8822

<400> SEQUENCE: 10
ggcggagcac acgcaaaatt gg                                              22

<210> SEQ ID NO 11
<211> LENGTH: 22
<212> TYPE: DNA
<213> ORGANISM: GBV-B-like virus
<220> FEATURE:
<221> NAME/KEY: primer_bind
<222> LOCATION: (1)..(22)
<223> OTHER INFORMATION: Primer SGB57 for region 8961-8982

<400> SEQUENCE: 11
tgcagaagtt tcttgtgaag ta                                              22

<210> SEQ ID NO 12
<211> LENGTH: 22
<212> TYPE: DNA
<213> ORGANISM: GBV-B-like virus
<220> FEATURE:
<221> NAME/KEY: primer_bind
<222> LOCATION: (1)..(22)
<223> OTHER INFORMATION: Primer AGB1 for region 9143-9122

<400> SEQUENCE: 12
cacatcgcgg ggtcgttaag cc                                              22

<210> SEQ ID NO 13
<211> LENGTH: 22
<212> TYPE: DNA
<213> ORGANISM: GBV-B-like virus
<220> FEATURE:
<221> NAME/KEY: primer_bind
<222> LOCATION: (1)..(22)
<223> OTHER INFORMATION: Primer AGB4 for region 8780-8761

<400> SEQUENCE: 13
ggaccgccct ggctttcttt cg                                              22

<210> SEQ ID NO 14
<211> LENGTH: 82
<212> TYPE: RNA
<213> ORGANISM: GBV-B-like virus

<400> SEQUENCE: 14
cgcugugcag agcguaguac caagggcugc accccgguuu uuguccaag cggagggcaa      60

```
ccccgcuug gaauuaaaaa cu                                                    82

<210> SEQ ID NO 15
<211> LENGTH: 70
<212> TYPE: RNA
<213> ORGANISM: GBV-A

<400> SEQUENCE: 15
ggcgcagugc acugcguaac ugaaggggug cacccccgguu gcccyacgcc cgauggcgur         60
guggucaauu                                                                 70

<210> SEQ ID NO 16
<211> LENGTH: 101
<212> TYPE: RNA
<213> ORGANISM: HCV

<400> SEQUENCE: 16
aaugguggcu ccaucuuagc ccuagucacg gcuagcugug aaagguccgu gagccgcaug         60
acugcagaga gugcugauac uggccucucu gcagaucaug u                            101
```

GBV SEQUENCE

The present invention relates to novel viral sequences and various uses thereof. In particular it is based on identification of a hitherto unrecognised sequence at the 3' end of the GBV genome. Nucleic acid with the sequence, or allelic variants and fragments thereof, are useful in providing viral vector constructs infective in tamarins. Hybrid viral vectors including HCV components can be provided including nucleic acid of the invention allowing for infection of tamarins as a suitable model for study of HCV and for testing agents for ability to inhibit HCV activity.

The hepatitis GB agent was first described by Deinhardt and co-workers (Deinhardt et al. 1967. J. Exp. Med), who inoculated tamarins, small primates of the Saguinus species, with a serum from a patient (whose initials were GB) affected by acute hepatitis. This serum induced hepatitis in all inoculated tamarins and was passaged serially in these animals. Only recently molecular characterization of this agent has been achieved (Simons et al. 1995. Proc. Natl. Acad. Sci.; Muerhoff et al. 1995. J. Virol.), showing that two distinct positive-strand RNA viruses, GB virus A and B (GBV-A, GBV-B), were associated with GB agent hepatitis.

Subsequently, it was shown that the two viruses could be passaged separately in tamarins and that GBV-A does not replicate in the liver whereas GBV-B causes hepatitis (Schlauder et al. 1995. J. Med. Virol.; Schlauder et al. 1995. The Lancet). The initial inoculum originates from humans, although formal proof that GBV-A and GBV-B are indeed human pathogens has yet to be obtained. Immune reactivity against GBV-A and GBV-B derived peptides has been found in humans (Pilot-Matias et al. 1996. J. Med. Virol.; Simons et al. 1995. Nature Medicine), but attempts to detect viral sequences in the reactive plasma have to date been unsuccessful (Simons et al. 1995. Nature Medicine).

Sequence analysis of GBV-A and GBV-B genomes suggested that they belong to the Flaviviridae family and are related to hepatitis C virus (HCV). Comparison of their open reading frame with that of different HCV strains shows from 26 to 33% identity at the amino acid sequence level. However, comparison of the hydropathy profiles suggests that, despite the little overall amino acid sequence identity, these viruses share similarity in protein structure (Muerhoff et al. 1995. J. Viral.; Ohba et al. 1996. FEBS Letters).

Of the two, the most closely related to HCV is GBV-B, not only for the sequence similarity but also for sharing functional characteristics, tissue tropism, since they are both hepatotropic viruses, and pathogenesis (Zuckerman et al. 1995. The Lancet; Simons et al. 1996. Viral Hepatitis Reviews). The hypothesis of a functional homology between proteins of the two viruses has been already validated, in the case of proteins with important enzymatic activity such as the NS3 serine protease, responsible of maturation of the viral polyprotein (Scarselli et al. 1997. J. Virology) and the RNA dependent RNA polymerase NS5B protein responsible for the replication of the viral genome (unpublished data).

GBV-B may be used as a model for HCV with regard to infection and pathogenesis. In particular, HCV/GBV-B recombinant viruses may be used to evaluate the effect of antivirals directed against HCV targets of interest in vivo. This kind of approach requires the availability of a GBV-B genomic molecule able to replicate in vivo. The art has so far failed to provide this.

Only one GBV-B genomic sequence has been reported (GenBank Accession No. U22304) spanning 9143 nucleotides. The ORF of GBV-B shows a significant homology to the corresponding regions of HCV, and the potential secondary structure of GBV-B 5'-UTR shows a striking similarity to that of HCV (Lemon and Honda. 1997. Seminars in Virology). To date there are no reports of replication in vivo of any RNA based on this sequence.

The present invention is based at least in part on the identification of a novel nucleotide sequence, called GBV-B 3'X, that the inventors have found to be an integral part of the genome of GB virus B (GBV-B), corresponding to the 3'-terminus of the GBV-B genome.

In natural isolates this sequence is present: on both strands of GBV-B RNA, it was found in GBV-B RNA extracted from both serum and liver of tamarins and in GBV-B RNA extracted from at least two species of tamarins.

The putative secondary structure of this novel sequence resembles (particularly the 3'-terminal stem-loop structure) that of HCV, whose corresponding sequence has been proved to be essential for replication and infection (Kolykhalov et al. 1997. Science, 277: 570–574; Yanagi et al. 1999. Proc. Natl. Acad. Sci. USA, 96: 2291–2295).

The invention allows for this sequence to be used to confer infectivity in Tamarins.

Recombinant HCV/GBV-B viruses may be constructed carrying the HCV target genes of interest, i.e. for example a sequence coding for the NS3 protease, the NS5B polymerase, another single HCV protein (selected from E1, E2, NS2, NS4A, NS4B, and NS5A) or a combination of any of these, that are infective in tamarins, for example as described below.

A hybrid GBV/HCV comprising HCV NS3/4a represents one preferred embodiment of the invention. NS3/4a has been shown to cut the GBV sequence in the correct places. Other preferred embodiments comprise HCV helicase and/or polymerase.

At present, the only animal model for HCV infection is the chimpanzee. The limitations that this animal model implies, the chimpanzee being a protected species, make it inconvenient to use it in general and impossible for pharmacological studies in particular, where a large number of animals of small size is required. So far only a very limited number of chimpanzees per experiment has been experimentally infected with HCV to test infectivity of inocula and in trials for vaccine development.

The present invention makes it possible to infect small sized primates (tamarins) with recombinant GBV-B infectious RNA carrying HCV sequences encoding for HCV pharmacological targets. This means that it is possible to accomplish studies on anti-HCV antivirals in more suitable primates, thus overcoming the limitations in the number of animals to be used and dramatically reducing the cost of the experiments.

BRIEF DESCRIPTION OF THE FIGURES

FIG. 3 shows a partial sequence (SEQ ID NO:1) of the cDNA of the 3'-UTR region of GBV-B genome corresponding to nucleotides following poly-U tract. Nucleotides not present in the published sequence of GBV-B genome (GenBank Accession No. U22304) and providing a sequence in accordance with an aspect of the present invention are underlined. Numbering concerns only the portion corresponding to the GBV-B 3'X sequence. The position of the oligo 98145 used in PCR experiments is indicated by an arrow.

FIG. 4A shows predicted secondary structure of the complete GBV-B 3'-UTR, including the entire sequence following poly-U tract. The 3'X novel sequence spans from nt 51 to 309. The nucleotide sequences was subjected to elaboration with the program "Mfold" of the GCG (Genetics Computer Group) Sequence Analysis Package (Version 9.1) using default parameters (see below). The graphical output was produced by the program "Plotfold" of GCG.

FIG. 4B shows comparison of the putative secondary structure of the 3'-end region of GBV-A (SEQ ID NO:15), GBV-B (SEQ ID NO:14) and HCV (SEQ ID NO:16) encompassing 3'-stem-loops (3'-SL I, 3'-SL II and 3'-SL III). In 3'-SL II of GBV-B and GBV-A the identical nucleotides positions are indicated as white symbols on black dots background. GBV-B and HCV structures start at the nucleotide following poly-U; GBV-A, lacking a poly-U tract, starts at a position chosen to highlight the similarity with the GBV-B structure.

FIG. 5 shows results of experiments demonstrating GBV-B infection of *S. oedipus* tamarins upon intrahepatic injection of RNA transcript from plasmid FL-3. RNA transcribed from linearized FL-3 plasmid DNA was injected into the liver of tamarins B223 and 95-59. The graphic lines represent ALT levels. Minus and plus symbols below the graphic indicate absence or presence of GBV-B RNA respectively, as detected by RT-PCR.

According to one aspect of the present invention there is provided an isolated GBV polynucleotide which on ligation to the 3'-end of a GBV-B RNA molecule spanning the published sequence (GenBank Accession No. 22304) provides a viral RNA infective in a tamarin.

A further aspect provides a polynucleotide consisting essentially of a fragment of the sequence shown in FIG. 3 (SEQ ID NO:1) and/or the complement thereof, which fragment confers infectivity in a tamarin on a polynucleotide otherwise non-infective in the tamarin.

Viral nucleic acid which has "infectivity" or is "infective" is generally capable of replicating itself and preferably of producing viral particles able to infect host cells and to multiply by alternate cycles of entry into host cells and replication. The infectivity of tamarins by GBV-B (replication and amplification of input RNA and formation of viral particles that undergo secretion into the bloodstream) can be monitored by RT-PCR of RNA extracted from serum and/or by the pathogenic effects on the host (in the specific case, elevation of hepatitis markers, transaminases, in particular ALT).

Preferably the polynucleotide has a sequence from the non-coding regions of the genome of any GBV virus, which may include a GBV-A sequence.

Variants, especially "allelic" variants which may represent different strains or isolates, are likely to differ slightly in sequence from that shown in FIG. 3 (SEQ ID NO:1), and may have 1, 2, 3, 4, 5, 6, 7, 8, 9, 10, 10–15, 15–20, or more nucleotide substitutions, additions or deletions compared with the sequence shown, perhaps up to around 20% of the nucleotides. "Matched" substitutions will allow for maintenance of the secondary structure, where nucleotides that pair in hairpin loop structures may be exchanged without disrupting the hairpin loop.

The sequence of a variant of the sequence disclosed herein may have a certain % identity with the sequence of FIG. 3 (SEQ ID NO:1)which may be as defined and determined by the BLASTN program of Altschul et al. (1990) *J. Mol. Biol.* 215: 403–10, which is part of the Wisconsin Package, Version 9.1, (Genetics Computer Group, 575 Science Drive, Madison, Wis., USA, Wisconsin 53711). Preferably sequence comparisons are made using FASTA (see Pearson & Lipman, 1988. Methods in Enzymology 183: 63–98). Parameters are preferably set, using the default matrix, with the following: Gapopen (penalty for the first residue in a gap): −12 for proteins/−16 for DNA; Gapext (penalty for additional residues in a gap): −2 for proteins/−4 for DNA; KTUP word length: 2 for proteins/6 for DNA.

Preferably, a variant nucleic acid sequence shares at least about 60%, or 70%, or 80% homology, most preferably at least about 90%, 95%, 96%, 97%, 98% or 99% homology or identity. As noted, an allelic variant will have few changes from the sequence shown.

Relatedness of sequences may be determined by means of hybridisation under suitably stringent conditions.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5×Denhardt's reagent, 0.5–1.0% SDS, 100 $\mu$g/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al. 1989): $T_m$=81.5° C.+16.6Log [Na+]+0.41 (% G+C)−0.63 (% formamide)−600/#bp in duplex.

As an illustration of the above formula, using [Na+]=[0.368] and 50- % formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

Figure 1:
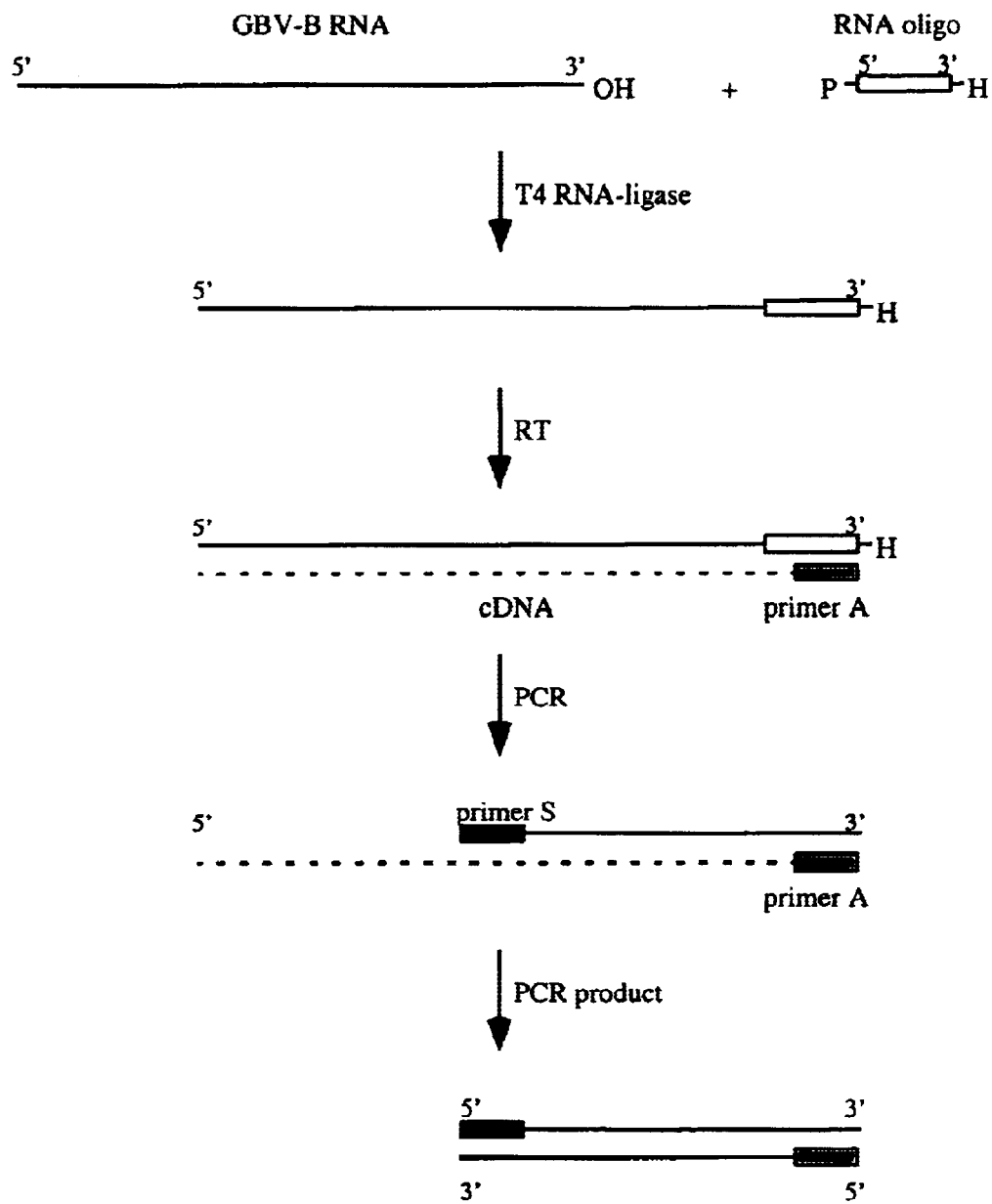
FIG. 1 shows a schematic representation of the experimental procedure used for the identification of the 3'X sequence of GBV-B genome. RNA oligo is oligo 96934 (SEQ ID NO:6); primer A (antisense) and primer S (sense) correspond to primers 98094 (SEQ ID NO:7) and SGB56 (SEQ ID NO:10) described elsewhere herein.
Figure 2:
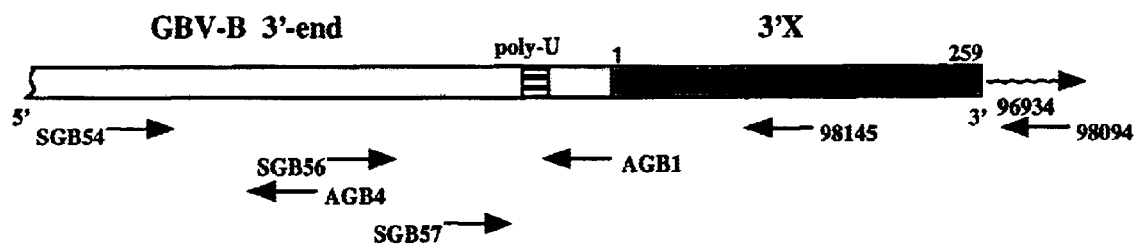
FIG. 2 shows a schematic representation of the GBV-B sequence with position and orientation of the oligonucleotides. Numbering refers to the 3'X sequence; nt 1 of this sequence immediately follows nt 9143 of the published sequence. Arrows indicate sense and approximate position of the primers used.

In one aspect the present invention provides an isolated polynucleotide consisting essentially of the following sequence (SEQ ID NO:2):

5'-AGUUUGGCGACCAUGGUGGAUCAGAACCGU
UUCGGGUGAAGCCAUGGUCUGAAGGGGAU
GACGUCCCUUCUGGCUCAUCCACAAAAACC
GUCUCGGGUGGGUGAGGAGUCCUGGCUGUG
UGGGAAGCAGUCAGUAUAAUUCCCGUCGUG
UGUGGUGACGCCUCACGACGUACUUGUCCG
CUGUGCAGAGCGUAGUACCAAGGGCUGCAC
CCCGGUUUUUGUUCCAAGCGGAGGGCAACC
CCCGCUUGGAAUUAAAAACU-3'

A further aspect provides a complement of this RNA sequence, that is the following sequence (SEQ ID NO:3):

5'-AGUUUUUAAUUCCAAGCGGGGGUUGCCCUC
CGCUUGGAACAAAAACCGGGGUGCAGCCCU
UGGUACUACGCUCUGCACAGCGGACAAGUA
CGUCGUGAGGCGUCACCACACACGACGGGA
AUUAUACUGACUGCUUCCCACACAGCCAGG
ACUCCUCACCCACCCGAGACGGUUUUUGUG
GAUGAGCCAGAAGGGACGUCAUCCCCUUCA
GACCAUGGCUUCACCCGAAACGG UUCUGAU
CCACCAUGGUCGCCAAACU-3'

A further aspect also provides the DNA sequence, corresponding to the 3' NTR element in the positive sense GBV-B genome RNA, containing or consisting essentially of the following sequence (SEQ ID NO:4):

5'-AGTTTGGCGACCATGGTGGATCAGAACCGT
TTCGGGTGAAGCCATGGTCTGAAGGGGATG
ACGTCCCTTCTGGCTCATCCACAAAAACCG
TCTCGGGTGGGTGAGGAGTCCTGGCTGTGT
GGGAAGCAGTCAGTATAATTCCCGTCGTGT
GTGGTGACGCCTCACGACGTACTTGTCCGC
TGTGCAGAGCGTAGTACCAAGGGCTGCACC
CCGGTTTTTGTTCCAAGCGGAGGGCAACCC
CCGCTTGGAATTAAAAACT-3'

A further aspect provides a complement of this DNA sequence, corresponding to the 3' NTR element in the negative sense GBV-B genome RNA, containing or consisting essentially of the following sequence(SEQ ID NO:5):

5'-AGTTTTTAATTCCAAGCGGGGGTTGCCCTC
CGCTTGGAACAAAAACCGGGGTGCAGCCCT
TGGTACTACGCTCTGCACAGCGGACAAGTA
CGTCGTGAGGCGTCACCACACACGACGGGA
ATTATACTGACTGCTTCCCACACAGCCAGG
ACTCCTCACCCACCCGAGACGGTTTTTGTG
GATGAGCCAGAAGGGACGTCATCCCCTTCA
GACCATGGCTTCACCCGAAACGGTTCTGAT
CCACCATGGTCGCCAAACT-3'

Further individual aspects of the invention provide a nucleic acid molecule either RNA or corresponding DNA with T substituted for U, which comprises or consists essentially of full-length GBV-B genome RNA followed by a poly(U) tract followed by a 309 nucleotide 3' terminal RNA sequence element containing the relevant sequence identified above, or with the relevant (complement) sequence 5' to a full-length GBV-B negative sense RNA or DNA, as appropriate.

Further individual aspects of the invention provide any such nucleic acid comprising or consisting essentially of a full-length GBV-B genome (or complement, and either RNA or corresponding DNA) in which a HCV sequence (e.g. encoding a HCV protein) is substituted for GBV-B sequence.

A further aspect provides an isolated polynucleotide consisting essentially of the nucleotide sequence and/or complement of the nucleotide sequence shown in FIG. 3 (SEQ ID NO:1).

A further aspect provides an isolated polynucleotide consisting essentially of the sequence of nucleotides underlined in FIG. 3 and/or the complement.

A variant or fragment of the full sequence identified herein preferably retains secondary structure substantially the same as shown in FIG. 4A or FIG. 4B for polynucleotides of the invention, as determined using Mfold and Plotfold with parameters as noted below.

A polynucleotide in accordance with any aspect of the invention may be included in a larger nucleic acid molecule. In particular, the polynucleotide may be included in a molecule which includes one or more non-GBV, or non-GBV-B, sequences. It may be provided in a construct including any sequence foreign or heterologous to GBV or GBV-B-and which is of interest.

A polynucleotide in accordance with any aspect of the present invention may be provided in a construct including one or more HCV sequences.

A vector can be provided formed by the HCV genomic sequence lacking at least the 3'-end 101 nt, that is the 3'X conserved part (see Yanagi et al. 1999. Proc. Natl. Acad. Sci. USA), FIGS. 2B–3, replaced by the GBV-B 3'X sequence comprising at least about 82 nt of its 3'-end, see FIG. 2B–2.

Vectors can be provided in which single genes for HCV proteins or combination of genes for HCV proteins are substituted to the equivalent genes of GBV-B in the complete GBV-B genome with 3'X.

A polynucleotide in accordance with any aspect of the present invention may be provided in a replicable vector.

Generally, a polynucleotide according to the present invention is provided at the 3' terminus of a strand of nucleic acid (or at the 5' terminus where it is a complement, as noted above).

A polynucleotide in accordance with any aspect of the present invention may be provided in a nucleic acid packaged within a viral particle, especially a HCV particle.

A host cell containing a polynucleotide of the invention represents a further aspect of the invention.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and virus infection.

Nucleic acid is generally provided as DNA or RNA, though may include one or more nucleotide analogues, and may be wholly or partially synthetic. Nucleic acid molecules and vectors according to the present invention may be provided in isolated and/or purified form, e.g. in substantially pure or homogeneous form. The term "isolate" may be used to reflect all these possibilities. Where a DNA sequence is specified, e.g. with reference to a figure, unless context requires otherwise the RNA equivalent, with U substituted for T where it occurs, is encompassed, and vice versa (unless context demands otherwise).

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

A further aspect of the invention provides a method of infecting a primate, especially a tamarin, with a viral vector which includes a polynucleotide of the invention. Preferably the polynucleotide of the invention confers on the viral vector the ability to replicate in the primate, especially tamarin. The viral vector may be in the form of an RNA transcribed from a plasmid including the whole GBV-B sequence, that corresponding to GenBank Accession. No. 22304 or variants of it, to the poly-U and followed by the sequence described in FIG. 3 (SEQ ID NO:1), including the extra C (in position -7 in FIG. 3) and the 259 nt novel 3'X sequence underlined.

A further aspect provides an assay method for an agent which inhibits GBV infection or activity, which method includes administering a test substance to a primate infected with hybrid HCV comprising a polynucleotide in accordance with the present invention, and determining effect of the test substance on infection in the primate and/or other GBV activity.

A further aspect provides an assay method for an agent which inhibits HCV infection or activity of an HCV component, e.g. the NS3 protease, the NS5B polymerase etc, which method includes administering a test substance to a primate infected with hybrid HCV comprising a polynuclectide in accordance with the present invention, and determining effect of the test substance on infection in the primate and/or activity of a said HCV component.

Preferably an agent that inhibits the infection or activity is identified. This may be by testing the effect of the substance administration on the parameters of infection such as viral RNA detection, one or more disease markers (such as ALT levels) and/or presence of anti-viral antigen antibodies, on groups of infected animals respect to a control group of animals not treated with the substance under examination.

Further assays in accordance with the present invention employ cells in culture that are infected or transformed with nucleic acid of the invention. GBV nucleic acid may be employed in assay methods for obtaining agents able to modulate GBV infection or activity, or in assay methods for obtaining agents able to modulate activity of an HCV component included in a GBV/HCV hybrid as disclosed.

Suitable end-points, which may be quantitated, include viral replication, presence of virus, and amount of GBV nucleic acid present.

Primarily, inhibitors are sought to be identified by means of assay methods in accordance with the present invention. However, ability of an agent to increase viral replication or activity of one or more viral components (e.g. a HCV component in a hybrid construct) may be shown by an increase in viral replication, presence of virus or amount of nucleic acid. Modulators provided by the present invention include not only inhibitors but also stimulators of viral replication of activity of a viral (e.g. HCV) component.

The test substance applied to the animal may already be suspected of having a desired inhibitory activity. It may have tested positive in one or more prior in vitro assays.

The test substance applied to the animal may have previously been subjected to pharmacological studies in order to design an appropriate specific protocol to test it for inhibition of viral infection.

The skilled person is readily able to design and utilise appropriate control experiments to rule out toxic or non-specific effects.

Following administration of a vector and/or test substance to a tamarin in accordance with the present invention, the animal may be sacrificed.

Following identification of a substance which modulates or affects the activity of interest, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified as a modulator of an HCV activity, in accordance with what is disclosed herein, but also a pharmaceutical composition, medicament, drug or other composition comprising such a substance, a method comprising administration of such a composition to a patient, e.g. for treatment (which may include preventative treatment) of HCV infection, use of such a substance in manufacture of a composition for administration, e.g. for treatment of inflammation or a cellular growth abnormality or other disease or condition as discussed, and a method of making a pharmaceutical composition comprising admixing such a substance with a pharmaceutically acceptable excipient, vehicle or carrier, and optionally other ingredients.

A substance identified using as a modulator of the activity may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptidesare not well suited as active agents for oral compositions as they tend to be quickly degraded by proteases in the alimentary canal. Mimetic design, synthesis and testing may be used to avoid randomly screening large number of molecules for a target property.

Mimetics of substances identified as having ability to modulate the desired activity using a screening method as disclosed herein are included within the scope of the present invention. A polypeptide, peptide or substance able to modulate an activity according to the present invention may be provided in a kit, e.g. sealed in a suitable container which protects its contents from the external environment. Such a kit may include instructions for use.

The present invention extends to use of an agent identified in an assay method as set out above, in providing a mimetic of the agent which retains the desired activity.

For a pharmaceutically useful compound identified according to the present invention that is to be given to an individual, administration is preferably in a "prophylactically effective amount" or a "therapeutically effective amount" (as the case may be, although prophylaxis may be considered therapy), this being sufficient to show benefit to the-individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Other aspects of the present invention provide for inhibition of GBV replication or infection, which may have therapeutic potential. An inhibitor of the function of the 3' sequence provided by the present invention may be employed. Such an inhibitor may inhibit interaction between negative and positive strand synthesis required for viral replication. Appropriate inhibitors include oligonucleotide fragments of the relevant region identified herein, or variants thereof which retain ability to hybridise specifically to a sequence of the invention to inhibit complementary strand synthesis. Further embodiments employ ribozymes, preferably of the hammerhead type, with sequences specifically designed to target the 3' sequence of the invention.

Thus, methods of treatment employing an inhibitor of GBV 3' sequence function, compositions comprising such an inhibitor and uses of such an inhibitor in the manufacture of a medicament are provided as further aspects of the invention.

Still further aspects employ probes or primers which hybridise within the 3' sequence of the invention (or complement as disclosed) in methods for determining the presence of GBV nucleic acid in a test sample, for instance in cells or a nucleic acid preparation derived from cells. This may be used in a laboratory context, for instance in verifying experimental protocols used in setting up assays as discussed above, or in a diagnostic context. Nucleic acid derived from an individual may be tested for the presence or absence of GBV nucleic acid including sequence of the invention. Suitable primers are disclosed herein, and others may be designed by those skilled in the art given the present disclosure and techniques available in the art. A probe or primer may be labelled in any appropriate way for detection in order to determine a positive result for the presence of target sequence in the test sample.

Further aspects and embodiments of the invention will be apparent to those skilled in the art in view of the present disclosure, including the following experimental

EXEMPLIFICATION

EXAMPLE 1

Identification and Characterisation of GBV 3' Sequence

The published sequence (GenBank Accession. No. U22304) was considered as the genomic full length sequence of GBV-B not only by the authors but also by the scientific community (Kolykhalov et al. 1997. Science, 277: 570–574; Honda et al. 1999. J. Virology, 73: 1165–1174).

However, the present inventors believed that the published 3'-UTR of GBV-B was not complete, and with the aim of constructing a GBV-B genomic molecule capable of sustaining infection in animals, decided to try to determine the sequence of the very 3'-end of the viral genome, that could be essential for replication, independently on the information available in literature.

They discovered a novel 259 nucleotides sequence located at 3'-end of the genome of GBV-B. This sequence is not included in the previously published sequence of GBV-B RNA (GenBank Accession No. U22304), it does not significantly resemble any known nucleotide sequence present in release 109.0 of GenBank and release 56.0 of EMBL (abridged) and none of the 6 translation frames of that sequence encodes any known protein.

In spite of the absence of sequence homology, the novel GBV-B sequence shows a potential secondary structure very similar to that of the corresponding part (3'X) of HCV genomic RNA, suggesting that the GBV-B structure function is the same as that of HCV.

The GBV-B novel sequence of the invention may play analogous roles to the HCV 3'-X sequence as an indispensable region for replication and/or assembly processes. The inclusion of this sequence in a GBV-B genomic cDNA molecule may be used to allow for infectious in vitro transcribed RNA and to construct viable chimeras between HCV and GBV-B genomes.

Identification of a novel sequence in the GBV-B genome. With the aim of identifying the very 3'-end of GBV-B, RNA was prepared from serum of an infected tamarin (B234) and ligated to the 26-mer RNA oligo, 96934 (5'-rArArArCrCrCUUrGrGrArCUrGrCrGrArCrGrGrCUrGrCrGrA-3') (SEQ ID NO:6) that had previously been subjected to modifications of 5' and 3' ends as described in the Materials and Methods section below. First strand cDNA synthesis was obtained by using as an antisense oligo the DNA oligo 98094(5'-GCAGCCGTCGCAGTCCAAGGG-3') (SEQ ID NO:7) complementary to part of the 96934 oligo sequence. cDNA was amplified by PCR using oligo 98094 (SEQ ID NO:7) in combination with SGB56 oligo of opposite polarity (SEQ ID NO:10), corresponding to nt 8801–8822 of the GBV-B published sequence (GenBank Accession No. U22304). PCR products were analyzed on 1.3% agarose gel and a faint but sharp band was visible. The band was eluted, cloned and sequenced with primers annealing in the vector sequence.

The sequence corresponding to SGB56 oligo was followed as expected by the published GBV-B genome sequence, with only one difference, an insertion of a C at position 9138. The already published sequence continued with a new sequence of 259 nt followed by the sequence corresponding to that of the RNA oligo 96934, as expected from the experimental procedure used. In FIG. 3 part of this sequence is shown spanning the portion downstream of the poly-U tract and including the whole novel sequence. The 259 nt novel sequence (FIG. 3) was defined "GBV-B 3'X" sequence by analogy to HCV 3'-end of genomic sequence.

By comparing the GBV-B 3'X nucleotide sequence with those of the 3'-end portion of GBV-A and GBV-C/HGV isolates it appears that only in a tract of 39 nt (corresponding to positions 178–216 of GBV-B 3'X sequence) an homology of 80% is present with the GBV-A sequence (GenBank Accession: No. 22303 last updating Sep. 30, 1996, NID g1572847); in the 3'-most stretch of 18 nt (199–216) of this sequence the homology raised to 94.4%. This last fragment also showed 94.1homology in 17 nt overlap with several isolates of GBV-C/HGV (for instance GenBank Accession. No. 36380). The rest of the sequence does not show significant homology.

The novel sequence (GBV-B 3'X) was used to search the most recent available release of the nt sequence databases (GenBank Release 109.0 (10/1998); EMBL (Abridged) Release 56.0 (09/1998) as provided by the Genetics Computer Group (GCG), Madison, Wis., without finding any significant homology to known sequences. Default parameters for FastA (Pearson and Lipman. 1988. Proc. Natl. Acad. Sci. USA 85; 2444–2448) as implemented in the GCG package were: Expect=2.0, Wordsize=6, Gapweight=16, Lengthweight=4. Default parameters for BLASTN (Version 1.4.7) (Altschul et al. (*J. Mol. Biol*. 215; 403–410 (1990) as implemented in the GCG package were: E=100.0, W=11, V=250.0, B=100.0. Matches to database sequences were considered to be significant if E-values were below 0.005 (FASTA) and below 0.01 (BLASTN), respectively (Anderson & Brass, CABIOS, 14; 349–356 (1998)). All potential translation products of the six frames in the novel sequence (where only one is a real ORF starting with a Met, 26 aa long, see above) have been used to search protein databases PIR-Protein, Release 57.0 (06/1998), and SWISS-PROT, Release 36.0 (07/1998), databases as provided by the Genetics Computer Group (GCG), Madison, Wis. using the BLASTX program. No significant match was detected (significance threshold P-values smaller than 0.01) for the only potential ORF present in the GBV-B 3'X sequence.

Moreover, the ORFs obtained translating nucleotide sequences databases quoted above were also compared to all the amino acid sequences that can be deduced from the nucleotide novel sequence. In none of these cases was a significant homology found. The general conclusion of this search is that the 259 nt sequence identified is in the overall a novel sequence that has never been described before.

Animals

*Saguinus fuscicollis* and *Saguinus oedipus* tamarins were the source of liver and blood serum.

RNA Preparation From Serum

RNA was prepared from serum samples using the QIAamp Viral RNA kit (Qiagen) by following the manufacturer's instructions. RNA obtained from 140 µl serum aliquots was eluted in 50 µl sterile water. In first strand CDNA synthesis reactions 10 µl aliquots were used.

RNA Preparation From Liver

A portion (360 mg) of resected tamarin liver infected by GBV-B was used to extract total RNA using Ultraspec II RNA isolation system (Biotecx), by following the manufacturer's instructions. Total recovery was 820 µg at 2.6 µg/µl concentration. RNA was also extracted from noninfected tamarin liver with the same procedure and the yield was 1.7 mg from 400 mg of tissue (final concentration 3.4 µg/µl). In first strand cDNA synthesis reactions 1 µl aliquots were used.

Oligonucleotides Synthesis and Modifications

Oligodeoxyribonucleotides were purchased from PRIMM, Milano (Italy). Oligoribonucleotide 96934 (SEQ ID NO:6) was obtained from Genset SA, (France). Oligoribonucleotide 96934 was modified for use in the RNA ligation reaction by blocking its 3'-end by oxidation and phosphorylating its 5'-end. 3'-end oxidation was performed by resuspending 1.25 nmole of dried oligo into 100 Fl of 50 mM Na acetate, pH 5.0 and incubating it for 1 hr at room temperature with 50 Fl of 100 mM NaIO$_4$. The oligo was then extracted with phenol/chloroform, purified by a Sephadex G-50 spun column, ethanol precipitated, subjected to two 70% ethanol washes and resuspended in 50 Fl sterile water. 20 Fl of the 3'-blocked RNA oligo were phosphorylated at the 5'-end by incubating it with 2 mM ATP, 10 units of T4 polynucleotide kinase and related buffer (Gibco-BRL) in 50 Fl volume for 1 hr at 371C. After phenol/chloroform extraction and ethanol precipitation in the presence of glycogen as carrier, the RNA oligo was resuspended in 50 Fl sterile water.

RNA Ligation Reaction.

10 µl aliquot of RNA extracted from serum of tamarin B234 was mixed with 10 Fl of 5'-phosphorylated/3'-blocked RNA oligo 96934 (SEQ ID NO:6)and with 6.5 Fl sterile water. After 3 min at 901C the mix was quickly chilled by immersion in an ice/water bath and briefly centrifuged at 41C. The following components of the ligation reaction were then added to the tube containing GBV-B RNA and RNA oligo in amounts suitable to reach the indicated concentrations in a final volume of 30 Fl: 10% DMSO, 50 mM Hepes pH 7.5, 20 mM MgCl$_2$, 3 mM DTT, 10 Fg/ml bovine serum albumin, 20 units RNasin (Promega), 0.1 mM ATP, 23.8 units of RNA ligase (Gibco-BRL). The reaction mixture was prepared in a 41C room keeping the sample on ice. Ligation reaction was performed by incubating the mixture at 41C for 24 hr. The reaction was stopped by incubation at 751C for 10 min, extracted with phenol/chloroform, then with chloroform and ethanol precipitated in the presence of 0.3 M Na Acetate pH 5 and glycogen as carrier. After washing with 70% ethanol, the sample was dried and resuspended in 20 Fl sterile water. 10 Fl of this sample were used for subsequent first strand cDNA synthesis.

First Strand cDNA Synthesis

RNA was used as a template for first strand cDNA synthesis in a 20 µl reaction. RNA was mixed with 10 pmoles antisense primer in a volume of 11 µl, denatured 5 min at 90° C., quickly chilled by immersion in an ice/water bathand centrifuged at 4° C. The following components of the reaction were then added to the tube in amounts suitable to reach the indicated concentrations: 2.56% DMSO, 20 units RNasin (Promega), Superscript buffer (Gibco-BRL), 10 mM DTT, 1.25 mM/each dNTPs. The reaction mixture was prepared in a 4° C. room keeping the sample on ice. The reaction was performed by pre-incubation of the mixture at 50° C. for 2 min followed by incubation with 1 µl Superscript II reverse transcriptase (Gibco-BRL) at 50° C. for 50 min. The reaction was stopped by incubation at 70° C. for 10 min.

PCR 2.5 µl aliquots of first strand cDNA synthesis reactions were added to a sterile 0.5 ml tube containing Elongase B buffer (Gibco-BRL), dNTPs (250 mM each), sense and antisense primer (200 nM each) in a total 50 µl volume; then 1 µl of Elongase mix (Gibco-BRL) was added, and finally 40 µl of mineral oil were stratified on top of reaction mixture by keeping the sample on ice. PCR were performed in a Perkin Elmer 9600 thermocycler by using the following conditions: 94° C. for 7 min (incubation of the reaction tube was initiated when the machine had reached 94° C., to obtain "hot start"), then 40 cycles of 94° C. for 1 min, 55° C. for 2 min, 68° C. for 2 min, followed by an extensive elongation step of 10 min at 68° C. 10 µl aliquots of reactions were analysed on 1.3% agarose gel in TAE running buffer (40 mM Tris pH 7.8, 5 mM Na acetate, 1 mM EDTA).

Cloning

PCR products were purified by cutting the band from agarose gel and eluting the DNA by electroelution followed by phenol extraction, chloroform extraction and ethanol precipitation. The purified PCR products were ligated by using the Original TA Cloning Kit (Invitrogen) into the 3' T-overhangs pCR2.1 vector supplied with the kit. This system allows direct ligation of PCR products to the vector.

Cloning of the sequences to be used as probes was done in pCR2.1 under T7 promoter control in both orientations in order to achieve strand specific synthesis of inserts by T7 polymerase in vitro transcription.

Sequencing

Sequencing was performed by dideoxy chain termination method (Sanger et al. 1977. Proc. Natl. Acad. Sci.).

Northern Blots 20 gg of total RNA samples were subjected to electrophoresis on a 1% agarose/formaldehyde gel, blotted onto Hybond−N+ membranes and hybridized to DNA or RNA probes. Electrophoresis, blot and hybridization procedures were performed by following the protocols of Amersham's Hybond−N+ membranes instruction manual. Radioactive DNA probes were prepared by using Amersham Megaprime kit following the manufacturer instructions. RNA probes were produced by in vitro transcription of constructs cloned under T7 promoter by T7 RNA polymerase in the presence of $^{32}$P-UTP.

Southern Blots

Tamarin genomic DNA was prepared by whole blood of non-infected tamarin B229 (*S. oedipus*) as described in Sambrook et al., Molecular cloning: a laboratory: manual, Second edition) and digested with BglII. Aliquots of 10 mg of digested DNA were separated on a 0.8% agarose gel, blotted and hybridized using Amersham Hybond N$^+$ membranes according to the manufacturer's instructions. Probes were prepared by labelling PCR fragments with Amersham Megaprime kit following the manufacturer's instructions.

RNA Secondary Structure Prediction

Secondary structure prediction was performed for the RNA sequence corresponding to the novel sequence, as well as HCV 3'X sequence, by running "Mfold" program of the GCG package. The output was produced by the program "Plotfold" of GCG.

The general algorithm used in the program Mfold for determining multiple optimal and suboptimal secondary structures is described by the author of the program, Dr. Michael Zuker (Science 244, 48–52 (1989)). A description of the folding parameters used in the algorithm is presented in Jaeger, Turner and Zuker (Proc. Natl. Acad. Sci. USA, 86, 7706–7710 (1989)).

There are several differences between the GCG implementation of MFold and Dr. Zuker's Mfold package. Dr. Zuker's lrna and crna programs, which fold linear and circular sequences, respectively, are combined into a single GCG program. By default, MFold treats the input sequence as a linear molecule. In Dr. Zuker's original implementation, the program takes an RNA sequence as input, computes the energy matrices, and then displays representations of optimal and suboptimal secondary structures. Dr. Zuker's program allows the option of storing the energy matrices in a save run of the program and later displaying the secondary structures in a separate continue run. The GCG version of MFold always saves the energy matrices into an output file. A separate program, PlotFold, reads these energy matrices and displays representative secondary structures. The default energy files are used by the program to predict folding at 37° C.

Mfold default parameters were: maximum size of interior loop=30; maximum loopsidedness of an interior loop=30; Temperature=37.0 degrees (Celsius) Plotfold default parameters: Plot base pairs at energy increment=5.7; point density=331.8 bases/100 platen units on each axis.

EXAMPLE 2

Rescue of the GBV-B Genomic Sequences by Using a Primer in the GBV-B 3'X Sequence To obtain direct evidence that the newly discovered sequence is actually part of the GBV-B genome, an experiment was performed to rescue GBV-B genome cDNA sequences from GBV-B RNA by using a primer whose sequence corresponds to part of the sequence under investigation. The source of RNA was the serum of the same tamarin (B234) used to perform the ligation experiment. RNA extracted from serum of the same tamarin bled before infection was used as a negative control. From these RNA preparations cDNA was prepared with oligo 98145 (5'-GCACAGCGGACAAGTACGTC-3') (SEQ ID NO:8) complementary to nt 166–185 of the novel sequence (see FIG. 3) and PCR performed with the same oligo and the sense oligo, SGB54 (SEQ ID NO:9), annealing at positions 8481–8502 of the known GBV-B sequence. The PCR products were analyzed on agarose gel: only GBV-B infected serum RNA gave rise to a PCR band product, as summarised in Table II.

The amount of product was not very high, probably due to the fact that the annealing of the primer for first strand cDNA synthesis was inefficient since it occurs in a region with a strong secondary structure. The band was eluted from gel, cloned and sequenced. The sequence corresponded to the GBV-B genome sequence from oligo SGB54 to the end of the published sequence and continued with the novel sequence of FIG. 3 until the region corresponding to the oligo 98145, as expected from the cloning procedure.

EXAMPLE 3

Rescue of the GBV-B 3'X Novel Sequence by Using a Primer in the GBV-B Published Sequence Analogous experiments have also been performed by synthesizing cDNA from the negative strand RNA of GBV-B with the sense oligo SGB54 (SEQ ID NO:9)and then performing PCR with SGB54 oligo in combination with 98145 (SEQ ID NO:8) or oligos hybridizing to the published sequence, such as AGB1 (SEQ ID NO: 12) and AGB4 (SEQ ID NO:13). RNA was produced from either serum or liver of two infected tamarins different from that used for the initial ligation experiment. As negative controls reactions using human serum as well as mock reactions were performed. As different negative controls, a primer complementary to the RNA oligo originally used in the RNA ligation experiment and a primer of the same polarity of SGB54 (oligo SGB57, SEQ ID NO:11), were used. As summarised in Table III, amplification was obtained only with GBV-B infected tamarin liver and serum samples, both using oligos in the published and in the novel sequence (AGB1-AGB4 and 98145 respectively).

The PCR products of the reactions with 98145 oligo were eluted from gel, cloned and sequenced. Also in this case the sequence corresponded to the GBV-B genome sequence from oligo SGB54 to the end of the published sequence and continued with the novel sequence of FIG. 3 to the part corresponding to the oligo 98145, as expected from the cloning procedure.

EXAMPLE 4

Localization of the GBV-B 3'X Sequence in GBV-B Infected Tamarin RNA by Northern Blot In order to confirm with a non-PCR based technique that the novel GBV-B 3'X sequence is present in the genomic RNA of GBV-B, Northern blot experiments were performed blotting tamarin liver total RNA. RNA extracted from GBV-B infected tamarin liver of two different species (*Saguinus fuscicollis* and *Saguinus oedipus*) was subjected to electrophoresis, blotted and hybridized using DNA probes corresponding to 3'X sequence or to a fragment of the same length encompassed by the published sequence (from nt 8800 to nt 9068), defined 3'-probe. As negative control, RNA from non-infected tamarin (*Saguinus fuscicollis*) liver was used.

The results show that 3'X probe hybrydizes to an RNA of the size expected for GBV-B genome, as evaluated from comparison with the size of the band enlightened with published sequence 3'-probe and by using an RNA size marker. The hybridization was specific since it only occurred with RNA extracted from GBV-B infected tamarins and not with the control RNA.

A Northern blot experiment was also performed blotting GBV-B infected tamarin liver RNA and using strand specific RNA probes (3'X-1 and 3'X-2 in the novel 3'X sequence, 3'-1 and 3'-2 in the published sequence). A band was present coincident with the viral RNA size with both 3'X probes, thus demonstrating that the novel 3'X is located in both GBV-B positive and negative strand genomic RNA. The signal was much stronger when the RNA probe complementary to that of sequence shown in FIG. 3 was used, that is probe 3'X-1. This is expected if this RNA probe hybrydizes to GBV-B genomic RNA (positive strand) that should be more abundant than replication intermediate form (negative strand). The ratio of the intensity of the signals obtained with the 3'X probes 3'X-1 and 3'X-2 of opposite polarity is the same of that obtained with the control sequence probes 3'-1 and 3'-2 (hybridizing to positive and negative strand of GBV-B RNA respectively). This result is a strong indication that the band visualized using the 3'X-1 and control 3'-1 probes and that visualized with the 3'X-2 and control 3'-2 probes correspond to the same molecular species, that is GBV-B positive and negative strand RNA respectively.

As well as the band corresponding to the size of viral genome, the probes specific for 3'X region also allow identification of a low molecular weight band, not revealed by the control probes. The presence of this l.m.w. band (of size ranging around 250–300 nt as far as it con be estimated from comparison with an RNA size marker) is linked to the presence of GBV-B RNA since it is evident only when infected tamarin liver RNA is used. This molecular species may be generated from GBV-B genome as a product of endonucleolytic processing and subsequently degraded or it can function as a mobile RNA element. GBV-B genomic RNA would exist in two forms, with and without the part of 3'X novel sequence corresponding to the l.m.w. species, at least in the liver. The complete genome including the novel sequence has to be present in at least part of the viral particles population as suggested by the original identification being obtained from virus-containing serum.

EXAMPLE 5

Search for the GBV-B 3'X Sequence in Genomic Tamarin DNA by Southern Blot

In order to exclude that the all or part of the 3'X sequence is encoded by tamarin genome and in order to exclude that the l.m.w. band identified with 3'X probes in Northern blots of tamarin liver RNA from infected animals corresponds to the transcript of a host gene induced by GBV-B infection, a Southern blotting experiment was performed with genomic DNA of *S.oedipus* tamarin. The specific probe was the same DNA fragment used in Northern blots corresponding to the 3'X region. As a negative control probe the DNA fragment corresponding to part of the published GBV-B sequence used in Northern blots was used as well. A positive control hybridization was performed with a DNA probe corresponding to part of the sequence of the CD81 receptor from *S.oedipus* tamarin (Scarselli et al.) of the same length of the GBV-B probes and labelled at the same specific activity. The stringency of all the hybrydization steps was comparable with that of Northern blots experiments.

The results of this experiment show that hybridization is obtained only with the tamarin CD81 receptor.gene probe, whereas both GBV-B probes did not give any signal. This indicates that the 3'X sequence is not encoded by tamarin DNA.

EXAMPLE 6

Prediction of Secondary Structure of the Novel Sequence.

Figure 4A:
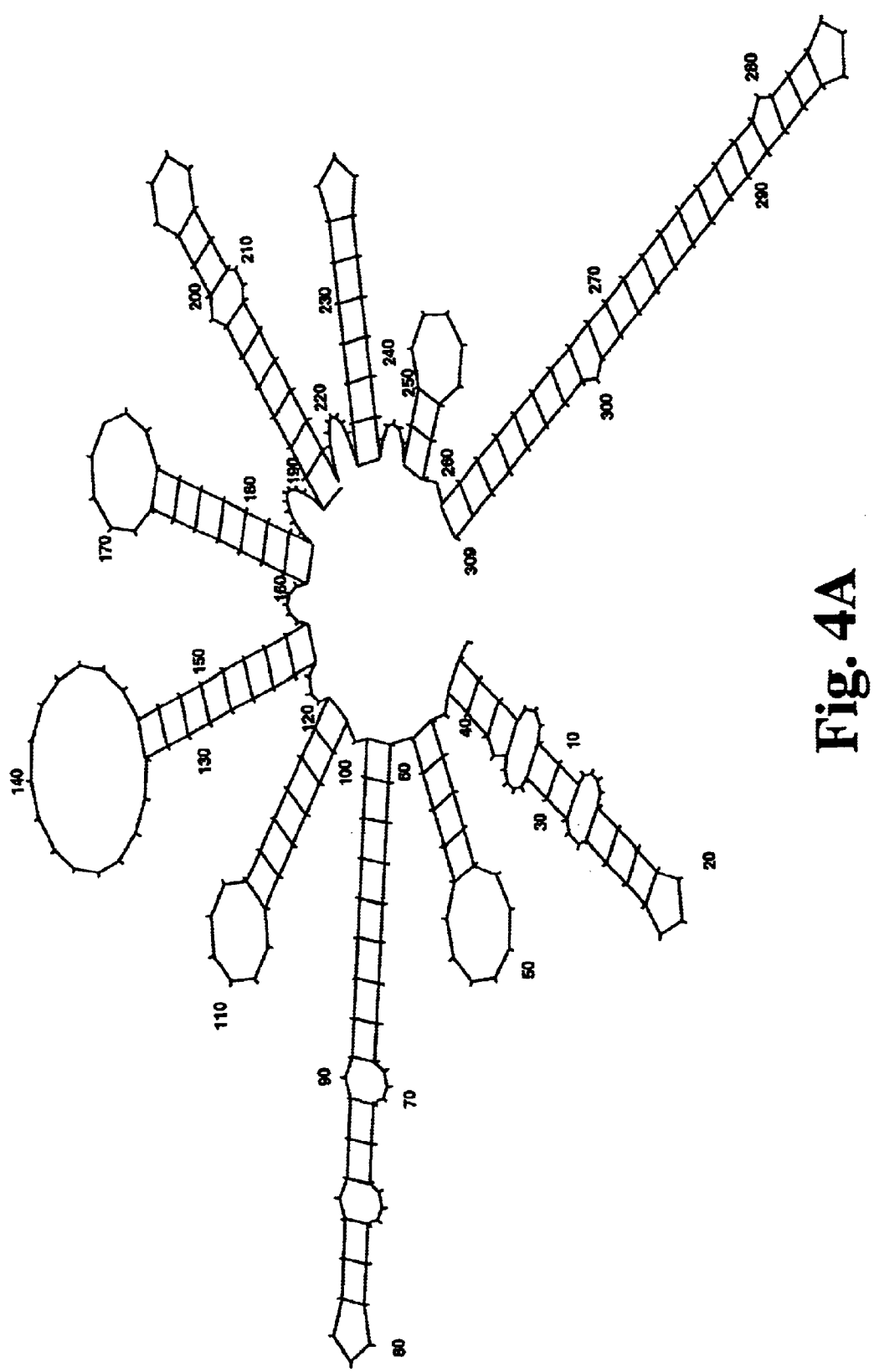

A prediction of secondary structure of the novel sequence was performed (FIG. 4A) showing a structure that in its $3^1$-most part resembles very much the 3'-end stem-loop structure of HCV genome (Tanaka et al. 1995. Biochem. Biophys. Res. Comm. Kolykhalov et al. 1996. J. Virology) in spite of the low sequence similarity, as shown in FIG. 4B. The features of this structure, as the distance between the two unpaired nt and the blunt end of the stem are unique to HCV among RNA viruses genomes known so far. In HCV experimental infections (Kolykhalov et al. 1997.; Yanagi et al. 1997. Proc. Natl. Acad. Sci.; Yanagi et al.1999. Proc: Natl. Acad. Sci.) infectivity has been demonstrated only for RNA genomic molecules transcribed from clones including this structure. Moreover this structure plays an important role also interacting with host proteins and by enhancing polyprotein translation (Tsuchihara et al. 1997. J. Virol. 1997; Ito et al. 1998. J. Virol.). In the region of the GBV-B 3'X spanning nt 178–216 a homology of 80% is present with GBV-A sequence (GenBank Accession No. 22303 and 18 nt of these sequence also show high homology with GBV-C/HGV. The corresponding sequences can be modelled in similar stem-loop structures, preceding the long stem-loop structure homologous to HCV 3'X. This implies that this portion of 3'X sequence can play a similar role in all GB viruses, and that the published sequences of GBV-A and GBV-C are incomplete, lacking the 3'-most stem-loop.

EXAMPLE 7

Experimental Infection of Tamarins

This confirms that the novel GBV-B 259 nt sequence is important to achieve viral infection and produce hepatitis in tamarins.

GBV-B RNA is transcribed from full length cDNA and tested for its capacity to infect tamarins and provoking hepatitis upon injection into the liver. Similar experiments have been successfully performed with hepatitis A viral RNA injected in marmosets liver (Emerson et al. 1992. J. Virol. 66: 6649–6654) and hepatitis C virus RNA injected in chimpanzee liver (Kolykhalov et al. 1997. Science, 277: 570–574; Yanagi et al. 1997. Proc. Natl. Acad. Sci. USA, 94: 8738–8743).

1. Animals

The study is carried out in 2 cottontop tamarins (*Saguinus oedipus*). The animals are purpose bred. Mature animals of 450–550 g are used. The animals meet the following criteria: in good physical health, free of GBV-B and GBV-C/HGV and have never been experimentally infected previously with related agents.

During the experiment the animals are housed separately, each animal in one cage. They are offered a daily diet consisting of rice, potatoes, eggs, fresh fruit and vegetables. Drinking water is available ad libitum via water bottle. The study is performed under biocontainment conditions at environmental temperatures.

2. Viral RNA Injection

Animals are intrahepatically inoculated with RNA in vitro transcribed from a cDNA construct spanning a full-length GBV-B genome followed by a poly(T) tract followed by a 309 nucleotide 3' terminal DNA sequence element containing the following sequence(SEQ ID NO:4):

5'-AGTTTGGCGACCATGGTGGATCAGAACCGT TTCGGGTGAAGCCATGGTCTGAAGGGGATG ACGTCCCTTCTGGCTCATCCACAAAAACCG TCTCGGGTGGGTGAGGAGTCCTGGCTGTGT GGGAAGCAGTCAGTATAATTCCCGTCGTGT GTGGTGACGCCTCACGACGTACTTGTCCGC TGTGCAGAGCGTAGTACCAAGGGCTGCACC CCGGTTTTTGTTCCAAGCGGAGG GCAACCC CCGCTTGGAATTAAAAACT-3'

Ten micrograms of a linearized plasmid encoding for GBV-B genome under the control of T7 promoter is in vitro transcribed by T7 RNA polymerase in a final volume of 100 µl under sterile conditions. The reaction is terminated by addition of 400 µl of sterile PBS without calcium or magnesium. Aliquots are frozen in dry ice and kept frozen at −80° C. until the moment of liver injection. Laparatomy is performed and three aliquots (0.15 ml each) of diluted transcription mixture are injected directly into the liver tissue at three sites in different lobes of the liver. The dosing/animal is the RNA transcribed from 5 µg of plasmid 3. Time Schedule The experiment is completed within 16 weeks from the infection. Blood samples are taken at 3 and 2 weeks pre-inoculation and at challenge date (t=0 weeks) to determine base-line ALT levels and ascertain GBV-B RNA absence. Then bleedings are performed weekly (1 ml of unheparinized blood) to monitor the serum ALT levels, GBV-B RNA and antibodies against GBV-B proteins. After 16 weeks animals are sacrificed and serum, liver, spleen and kidneys are harvested, and frozen for further analysis.

4. Observations Analyses and Measurements 4.1 Preparation of Serum

Blood samples are collected aseptically from the femoral or saphenous vein using Vacutainer blood collection tubes (Becton Dickinson, Vacutainer systems). The blood is allowed to clot for at least 30 min at room temperature and is then centrifuged for 10 min. at 1300 g. Serum is collected and immediately used for ALT level determination or stored frozen at −80 ° C. to be used for PCR analysis.

4.2 GBV-B RT-PCR

GBV-B specific RT-PCR is performed on serum and tissue samples.

4.3 Antibodies Anti-GBV-B Proteins Determination

Presence of antibodies against GBV-B antigens is assayed by conventional ELISA or protein immunoblotting using recombinant and synthetic GBV-B peptides.

4.4 Clinical Symptoms and General Behaviour

Behaviour and clinical symptoms (including appetite) are observed daily during the whole experiment by biotechnical personnel and recorded. Should an animal die during the test period a complete necropsy is carried out in which the abdominal and thoracic cavities and the skull are opened and internal organs examined in situ. Liver, spleen and kidneys are cryopreserved, as well preserved in neutral aqueous phosphate-buffered 4% solution of formaldehyde. All tissues are stored for future histopathological evaluation.

4.5 Body Weight and Temperature

Body weight and body temperature are measured before the start of the experiment and each time the animals are sedated for test substance administration and/or blood sample collection, immediately after sedation of each individual animal.

4.6 Criteria for Euthanasia

After developing acute hepatitis and remission, as indicated by variations in ALT levels and RNA levels, animals are sacrificed. As much blood as possible is sampled and left to clot for at least 30 min at room temperature. Serum is collected as described in 4.1., aliquotted and stored at −80 ° C. Liver, kidney and spleen are removed, processed and frozen at −80° C. Animals that do not show any signs of infection are sacrificed at the end of the study (week 16). As much blood as possible is sampled and left to clot for at least 2 hrs at room temperature. Serum is collected as described in 4.1.1., aliquotted and stored at −80 ° C. Liver, kidney and spleen are removed, processed and frozen at −80° C.

Only animals injected with the RNA including the novel sequence are positive for viral RNA and hepatitis markers.

In a first set of experiments it has been found that an RNA lacking the newly discovered sequence was unable to infect tamarins by intrahepatic injection.

A full-length GBV-B cDNA was constructed by RT-PCR amplification of RNA extracted from GBV-B infected tamarin liver and serum using oligos synthesized according to the published sequence U22304 (without the 3'X nucleic acid of the invention). Seven amplification fragments spanning the GBV-B genome were joined by conventional methodologies and cloned into the vector pACYC177 (Biolabs) downstream of the sequence of the T7 promoter obtaining the GBV-B full-length clone FL-1.

Ten micrograms of the linearized plasmid FL-1 were in vitro transcribed by T7 RNA polymerase in a final volume of 100 µl under sterile conditions. The reaction was terminated by addition of 400 µl of sterile PBS without calcium or magnesium. The RNA product was injected into the liver of two cotton-top tamarins (*Saguinus oedipus*) at three sites in different lobes of the liver. ALT levels and GBV-B RNA presence in the serum of the injected animals were monitored weekly for 16 weeks obtaining negative results.

EXPERIMENT 8

Experimental Infection of Tamarins with Infectious GBV

FL-1 DNA was sequenced and a sequence was obtained differing from that of published U22304 at the positions indicated in Table IV. Several of those differences had also been found in sequencing a number of GBV-B subgenomic clones obtained from independent RT-PCR amplifications of GBV-B infected sera or liver specimens in our laboratory.

The sequence was obtained of GBV-B starting from RNA of the liver of an animal (B234) whose serum was proved infectious in vivo. Un-cloned total PCR products and independent clones were sequenced in order to derive a consensus sequence. The differences in terms of nucleotides and amino acids of the B234 sequence respect to the U22304 and the FL-1 sequence are indicated in Table IV.

A further version of GBV-B genomic clone was constructed, correcting the nucleotides that in the FL-I sequence were responsible for amino acids substitutions with respect to the sequence derived from B234, plus one nucleotide substitution in position 9061 in the 3'-UTR. The mutagenesis was accomplished stepwise either by incorporating the desired nucleotides in PCR primers or by replacing mutated fragments with fragments obtained from subclones already available containing the desired nucleotides. The final construct, FL-3, also included the newly discovered 260 nucleotides (extra C in position 9137 and 259 nt of 3'X region). The complete sequence of clone FL-3 has been deposited in the EMBL Nucleotide Sequences Database under the accession number AJ277947. Nucleotides and amino acids variations of FL-3 respect to U22304, FL-1 and B234 sequences are shown in Table IV.

Figure 5:
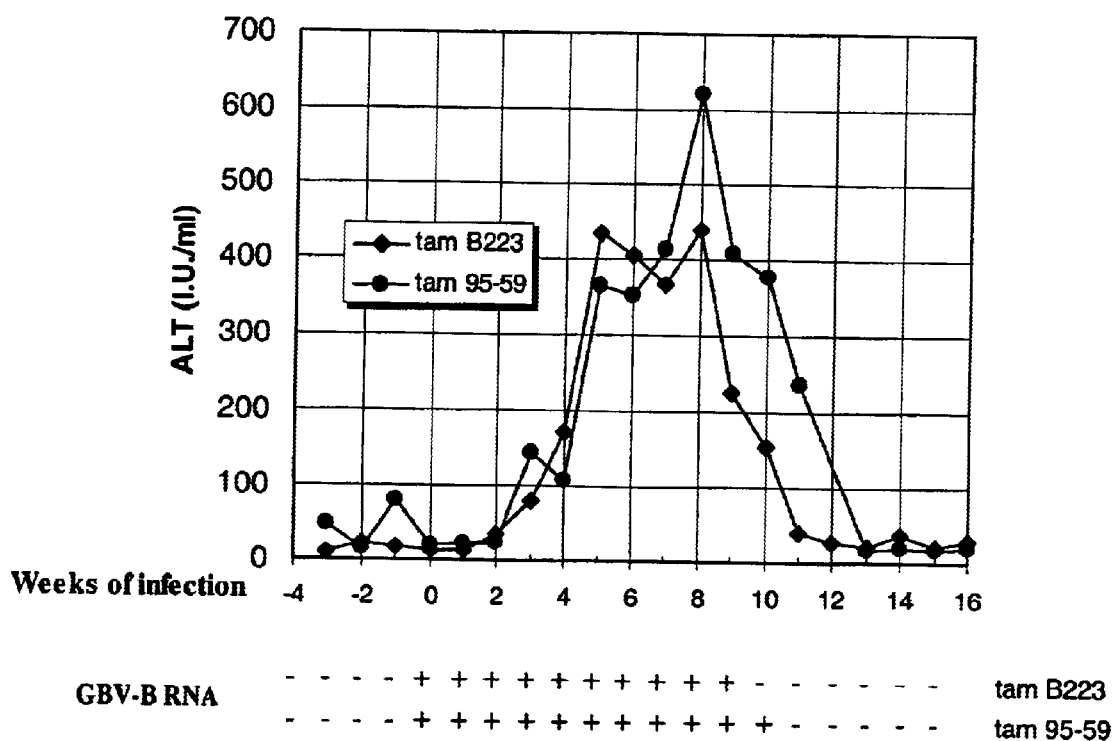

RNA transcribed from plasmid FL-3 was injected into the liver of two tamarins, B223 and 95-59, following the same protocol used in the previous experiments. Both injected Tamarins showed significant and durable ALT levels alteration and GBV-B RNA presence in the serum (see FIG. 5) demonstrating that the RNA transcribed from clone FL-3 containing the 3'X sequence is infective and replicates in these animals, provoking hepatitis.

REFERENCES

Caselmann. 1994. Antiviral Res, 24: 121–129.
Deinhardt et al. 1967. J. Exp. Med. 125: 673–687.
Emerson et al. 1992. J. Virology, 66: 6649–6654
Honda et al. 1999. J. Virology, 73: 1165–1174.
Ito et al. 1998. J. Virology, 72, 8788–8796.
Kolykhalov et al. 1997. Science, 277: 570–574.
Kolykhalov et al. 1996. J. Virology, 70: 3363–3371.
Lemon and Honda. 1997. Seminars En Virology, 8: 274–288.
Muerhoff et al. 1995. J. Virology. 69: 5621–5630.
Ohba et al. 1996. FEBS Letters, 378: 232–234.
Pilot-Matias et al. 1996. J. Med. Virol. 48: 329–338.
Sambrook et al. 1989. Molecular cloning: a lab. manual. Second edition
Sanger et al. 1977. Proc. Natl. Acad. Sci. USA, 74: 5463–5467.
Scarselli et al. 1997. J. Virology, 71: 4985–4989.
Schlauder et al. 1995. J. Med. Virol. 46: 81–90.
Schlauder et al. 1995. The Lancet 346: 447–448
Shimizu et al. 1990, Proc. Natl. Acad. Sci USA, 87:6441–6444.
Simons et al. 1996. Viral Hepatitis Reviews, 2, 229–246
Simons et al. 1995. Proc. Natl. Acad. Sci. USA, 92: 3401–3405.
Simons et al. 1995. Nature Medicine, 1: 564–569.
Tanaka et al. 1995. Biochem. Biophys. Res. Comm., 215: 744–749.
Tsuchihara et al. 1997. J. Virol., 71: 6720–6726.
Yanagi et al. 1997. Proc. Natl. Acad. Sci. USA, 94: 8738–8743.
Yanagi et al. 1999. Proc. Natl. Aced. Sci. USA, 96: 2291–2295
Zuckerman. 1995. The Lancet, 345: 1453–1454.

Table I shows nucleotide sequence of the oligonucleotide primers. The numbering of the oligos position refers to the GBV-B genome (GenBank Accession No. U22304), except for primer 98145 (SEQ ID NO:8) where the numbering refers to the position on the newly identified sequence 3'X.

TABLE I

| | | |
|---|---|---|
| 96934 (RNA): | 5'-AAACCCUUGGACUGCGACGGCUGCGA-3' | (SEQ ID NO:6) |
| 98094: | 5'-GCAGCCGTCGCAGTCCAAGGG-3' | (SEQ ID NO:7) |
| 98145: | 190-171(3'X), 5'-GCACAGCGGACAAGTACGTC-3' | (SEQ ID NO:8) |
| SGB54: | 8481-8502, 5'-GGATTGGGTATCTAATACATCA-3' | (SEQ ID NO:9) |
| SGB56: | 8801-8822, 5'-GGCGGAGCACACGCAAAA TTGG-3' | (SEQ ID NO:10) |
| SGB57: | 8961-8982, 5'-TGCAGAAGTTTCTTGTGAAGTA-3' | (SEQ ID NO:11) |
| AGB1: | 9143-9122, 5'-CACATCGCGGGGTCGTTAAGCC-3' | (SEQ ID NO:12) |
| AGB4: | 8780-8761, 5'-GGACCGCCCTGGCTTTCTTTCG-3' | (SEQ ID NO:13) |

TABLE II

| Source | GBV-B | Primers | Expected result | Observed result |
|---|---|---|---|---|
| Tamarin serum | + | a) 98145 b) SGB54 | + | + |
| Tamarin serum | − | a) 98145 b) SGB54 | − | − |
| mock | mock | a) 98145 b) SGB54 | − | − |

Note: the first oligo (a) in each couples of primers is used for 1st strand cDNA synthesis and determines the selection of the template strand.

TABLE III

| Source | GBV-B | Second Primer | Expected result | Observed result |
|---|---|---|---|---|
| Tamarin liver | + | AGB4 | + | + |
| Tamarin liver | + | AGB1 | + | + |
| Tamarin liver | + | 98145 | + | + |
| Tamarin liver | + | 98094 | − | − |
| Tamarin liver | + | SGB57 | − | − |
| Tamarin serum | + | AGB4 | + | + |
| Tamarin serum | + | AGB1 | + | + |
| Tamarin serum | + | 98145 | + | + |
| Tamarin serum | + | 98094 | − | − |
| Tamarin serum | + | SGB57 | − | − |
| Human serum | − | AGB4 | − | − |
| Human serum | − | 98145 | − | − |
| Human serum | − | 98094 | − | − |
| mock | mock | AGB4 | − | − |
| mock | mock | 98145 | − | − |
| mock | mock | 98094 | − | − |

Note: in all the combinations the first oligo in each couples of primers used for 1st strand cDNA synthesis was SGB54 and it determines the selection of the template strand.

TABLE IV

| genomic region | position nt (aa) | Nucleotides | | | | Amino acids | | | |
|---|---|---|---|---|---|---|---|---|---|
| | | U 22304 | FL-1 | FL-3 | B234 | U 22304 | FL-1 | FL-3 | B234 |
| 5'-UTR (1-445)* | | | | | | | | | |
| core (446–913) | 453 (3) | T | C | T | T | V | A | V | V |
| E1 (914–1489) | 1003 | C | T | T | T | | | | |
| | 1030 | C | T | T | T | | | | |
| | 1086 | A | G | A | A | | | | |
| | 1334 (297) | T | G | T | T | F | V | F | F |
| | 1448 | T | C | C | C | | | | |
| E2 (1490–2641) | 1726 | C | T | T | T | | | | |
| | 1875 (477) | A | T | A | A | Q | L | Q | Q |
| | 2562 (706) | C | A | A | A | P | H | H | H |
| | 2563 (706) | A | C | C | C | | | | |
| | 2566 | T | C | C | C | | | | |
| | 2625 (727) | C | T | T | T | A | V | V | V |
| NS2 (2642–3265) | 2674 (743) | A | G | A | A | I | M | I | I |
| | 2816 (791) | C | T | T | T | L | F | F | F |
| | 2818 | C | T | T | T | | | | |
| | 2855 (804) | A | G | G | G | T | A | A | A |
| | 2890 | T | T | C | T | | | | |
| | 2977 | T | C | C | T | | | | |
| NS3 (3266–5125) | 3473 (1010) | T | C | T | T | S | P | S | S |
| | 3483 (1013) | C | T | C | C | P | L | P | P |
| | 3616 | C | C | T | C | | | | |
| | 4114 | C | T | T | T | | | | |
| | 4117 | C | A | A | A | | | | |
| | 4177 | T | C | C | C | | | | |
| | 4615 | C | T | T | T | | | | |
| | 4867 | T | T | A | A | | | | |
| | 5014 | T | G | T | T | | | | |
| NS4A (5126–5290) | 5236 (1602) | T | C | T | T | V | A | V | V |
| | 5250 | T | C | T | T | | | | |
| NS4B (5291–6034) | 5329 | C | T | T | T | | | | |
| | 5332 | T | C | C | C | | | | |
| | 5350 | A | C | C | C | | | | |
| | 5788 | T | T | C | C | | | | |
| | 5812 | C | C | T | T | | | | |
| | 5989 (1848) | A | G | A | A | I | M | I | I |
| NS5A (6035–7267) | 6070 | T | T | C | C | | | | |
| | 6218 (1925) | T | C | T | T | C | R | C | C |
| | 6243 (1933) | T | C | T | T | V | A | V | V |
| | 6427 | T | T | C | C | | | | |
| | 6577 | G | T | T | T | | | | |
| | 6690 (2082) | T | C | C | C | I | T | T | T |
| | 6880 | T | T | C | T | | | | |
| | 6965 (2174) | T | C | C | C | S | P | P | P |
| | 6979 | T | C | T | T | | | | |
| | 7015 | A | G | G | G | | | | |
| | 7061 (2206) | A | G | A | A | T | A | T | T |
| | 7128 (2228) | G | A | A | A | G | E | E | E |
| | 7142 (2233) | A | G | G | G | T | A | A | A |
| NS5B (7268–7282) | 7282 | T | C | T | T | | | | |
| | 7483 | A | A | G | A | | | | |
| | 7675 | T | T | A | T | | | | |
| | 7744 | T | T | C | C | | | | |
| | 7849 | C | A | A | A | | | | |
| | 7913 (2490) | T | C | T | T | C | R | C | C |
| | 8155 | A | G | A | A | | | | |
| | 8233 | G | G | A | G | | | | |
| | 8361 (2639) | C | T | C | C | S | I | S | S |
| | 8440 | G | A | G | G | | | | |
| | 8539 | C | T | C | C | | | | |
| | 8942 (2833) | G | A | G | G | V | I | V | V |
| | 8971 | T | T | T | T | | | | |
| 3'-UTR (9038– | 9061 | T | C | C | C | | | | |
| | Poly-U | 27 | 21 | 21 | 21 | | | | |
| | da nt ins. 9136–9137* | — | — | C | C | | | | |
| | 9316 | n.a. | n.a. | C | C | | | | |
| | 3'X sequence | — | — | + | + | | | | |

*(amino acid residue positions of putative protein boundaries)
** = C9137, from this nt numbering is increased of one unit respect to that of U22304.

What is claimed is:

1. An isolated polynucleotide comprising a nucleotide sequence provided by the RNA version of SEQ ID NO: 1 wherein U is substituted for T, or a derivative of the RNA version of SEQ ID NO: 1 having no more than 10 alterations from the RNA version of SEQ ID NO: 1, wherein said nucleotide sequence enables a GBV-B genome lacking a 3' UTR following its 3' poly U tract to infect a tamarin when said nucleotide sequence is ligated to the 3'end of said GBV-B genome, provided that each of said alterations is either a nucleotide substitution, addition, or deletion.

2. The isolated polynucleotide of claim 1, wherein said derivative has no more than 4 alterations from the RNA version of SEQ ID NO: 1.

3. The isolated polynucleotide of claim 1, wherein said derivative has no more than 2 alterations from the RNA version of SEQ ID NO: 1.

4. An isolated polynucleotide comprising a nucleotide sequence selected from the group consisting of: SEQ ID NO: 2, the DNA version of SEQ ID NO: 2 wherein T is substituted for U, the complement of SEQ ID NO: 2, and the complement of the DNA version of SEQ ID NO: 2.

5. The isolated polynucleotide of claim 4, wherein said nucleotide sequence is SEQ ID NO: 2.

6. The isolated polynucleotide of claim 5, wherein said polynucleotide is a tamarin infective GBV-B genome.

7. The isolated polynucleotide of claim 4, wherein said polynucleotide consists of said nucleotide sequence.

8. A DNA vector comprising a nucleotide sequence of either SEQ ID NO: 1 or a derivative of SEQ ID NO: 1 having no more than 10 alterations from SEQ ID NO: 1, wherein the RNA version of said nucleotide sequence enables a GBV-B genome lacking a 3' UTR following its 3' poly U tract to infect a tamarin when said nucleotide sequence is ligated to the 3'end of said GBV-B genome, provided that each of said alterations is either a nucleotide substitution, addition, or deletion.

9. A host cell transformed with the vector of claim 8.

10. The vector of claim 8, wherein said derivative has no more than 4 alterations from SEQ ID NO: 1.

11. A host cell transformed with the vector of claim 10.

12. The vector of claim 8, wherein said derivative has no more than 2 alterations from SEQ ID NO: 1.

13. A host cell transformed with the vector of claim 12.

14. The vector of claim 12, wherein said vector is a plasmid vector.

15. A host cell transformed with the vector of claim 14.

16. A DNA vector comprising a nucleotide sequence selected from the group consisting of: the DNA version of SEQ ID NO: 2 wherein T is substituted for U and the complement of the DNA version of SEQ ID NO: 2.

17. A host cell transformed with the vector of claim 16.

18. The vector of claim 16, wherein said nucleotide sequence is the component of the DNA version of SEQ ID NO: 2.

19. A host cell transformed with the vector of claim 18.

20. The vector of claim 18, wherein said vector comprises DNA that codes for a tamarin infective GBV-B genome comprising the RNA version SEQ ID NO: 1.

21. A host cell transformed with the vector of claim 20.

22. The vector of claim 16, wherein said vector is a plasmid.

23. A host cell transformed with the vector of claim 22.

24. An isolated polynucleotide comprising a nucleotide sequence that can hybridize to the complement of SEQ ID NO: 1 under hybridization conditions providing an overnight hybridization at 65° C. in 0.25 M Na$_2$HPO$_4$, pH 7.2, 6.5% SDS, 10% dextran sulfate and a final wash at 60° C. in 0.1×SSC, 0.1% SDS, wherein said nucleotide sequence enables a GBV-B genome lacking a 3' UTR following its 3' poly U tract to infect a tamarin when said nucleotide sequence is ligated to the 3'end of said GBV-B genome.

* * * * *